United States Patent [19]
Glassman

[11] Patent Number: 5,170,804
[45] Date of Patent: Dec. 15, 1992

[54] MAYO-STAND DISPOSABLE DRAPE

[76] Inventor: Jacob A. Glassman, 1680 Michigan Ave., Miama Beach, Fla. 33139

[21] Appl. No.: 704,669

[22] Filed: May 20, 1991

Related U.S. Application Data

[63] Continuation-in-part of Ser. No. 655,767, Feb. 14, 1991, abandoned.

[51] Int. Cl.$^5$ .............................................. A61B 19/00
[52] U.S. Cl. .................................................... 128/849
[58] Field of Search ............... 128/846, 849, 851, 852, 128/855, 854

[56] References Cited

U.S. PATENT DOCUMENTS

| | | | |
|---|---|---|---|
| 3,542,019 | 11/1970 | Gittins | 206/440 X |
| 3,738,405 | 6/1973 | Ericson | 128/852 X |
| 3,770,119 | 11/1973 | Hultberg et al. | 206/439 |
| 4,042,109 | 8/1977 | Barcan | 206/440 |
| 4,595,102 | 6/1986 | Cianci et al. | 206/370 X |
| 4,596,245 | 6/1986 | Morris | 128/852 |

Primary Examiner—Robert A. Hafer
Assistant Examiner—Brian E. Hanlon
Attorney, Agent, or Firm—R. M. Saccocio

[57] ABSTRACT

A disposable drape for a Mayo stand is disclosed. The drape includes a built-in tray which is disposable along with the drape. The tray is compartmentalized to receive various shaped surgical instruments. One or more flaps are provided adjacent the edges of the tray. The flaps cover entrances to an opening under the Mayo stand and the upper body of a patient where surgical tools invariably become lost.

10 Claims, 3 Drawing Sheets

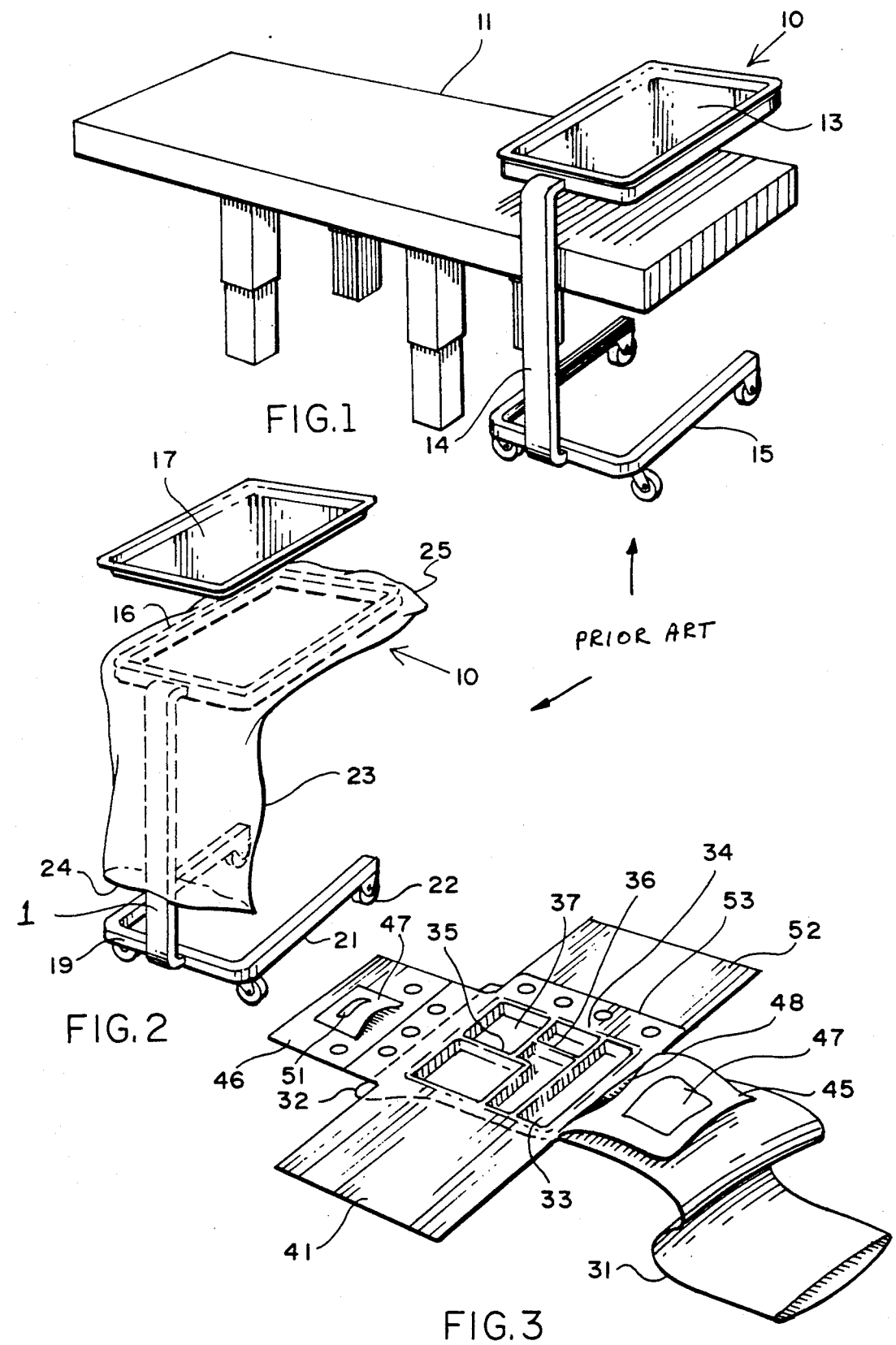

MAYO-STAND DISPOSABLE DRAPE

CROSS-REFERENCE TO RELATED APPLICATIONS

This application is a continuation-in-part of prior application Ser. No. 655,767, filed Feb. 14, 1991, by Jacob A. Glassman, entitled "A Mayo-Stand Disposable Drape Combined with Instrument Tray" and now abandoned.

BACKGROUND OF THE INVENTION

1. Field of the Invention

This invention relates in general to the field of disposable surgical drapes which are adaptable to fit over and around a Mayo stand and in particular to a disposable drape for a Mayo stand which includes a built-in instrument tray and one or more side flaps which are useful for closing off the undesirable open space between the draped body of a patient and a Mayo stand.

2. Description of the Prior Art

A Mayo stand is a portable stand having a horizontal frame within which a tray for holding surgical instruments may be placed; the horizontal frame is mounted to a vertical support member with horizontal legs attached to the bottom thereof. In side view, the shape of the Mayo stand is that of an approximate open "C" which shape allows the Mayo stand tray to be fitted over the lower end of a surgical table. The legs of the Mayo stand are typically provided with wheels to provide ease of maneuverability with respect to the surgical table. The C-shape of the surgical stand allows the horizontal tray to be fitted over the foot end of a patient or the surgical table so that the tray is readily accessible to a nurse who hands instruments to the operating surgeon, which instruments were initially on the tray of the Mayo stand.

A surgical prior art drape for the Mayo stand comprises an elongated, tubular bag which fits over the horizontal tray portion of the Mayo stand as well as the vertical support section of the Mayo stand. The typical prior art drape for the Mayo stand also resembles an elongated pillow case. Typically, the prior art drape is sterilized and disposable. The tray of the Mayo stand typically includes slightly raised side edges so that when covered by the Mayo-stand drape, a sterile, covered tray is provided on which may be positioned the surgical instruments which will be used by the operating surgeon during the operation. The nurse assisting the operating surgeon places the surgical instruments on top of the tray and especially within the depressed surface of the tray portion in an orderly manner so as to be readily accessible to the surgical nurse who removes the instruments and hands them to the operating surgeon when needed by the operating surgeon.

When the operating surgeon is through using a particular instrument, he gives the same back to the assisting nurse who then replaces the instrument back on the tray for later use. Typically, however, the operating surgeon puts the used instrument on the draped body of the patient rather than directly handing the same to the assisting nurse. In this manner, the assisting nurse can replace the used surgical instruments during a time period when she is not handing an instrument to the operating surgeon.

Unfortunately, some of the used instruments placed on the draped body of the patient slide down into the space between the Mayo stand and the foot portion of the draped body of the patient before the assisting nurse has the opportunity to replace the same on the tray. These instruments become lost. Lost instruments during a surgical operation is a very significant problem and causes unnecessary crises.

Accordingly, the primary purpose of a Mayo stand and drape is to provide a sterilized tray for the orderly placement thereon of surgical instruments at a location which is conveniently located to allow efficient handing of the different surgical instruments as needed by the surgeon throughout the surgery. While the prior art Mayo-stand drape has been successfully used to allow the performance of the basic essential needs of the operating surgeon, there are a number of disadvantages associated with the prior art Mayo-stand drape. Elimination of these disadvantages would further improve the efficiency and use of a Mayo stand surgical drape. For example, the main disadvantage of the prior art Mayo-stand drape is that a dead-air space or pocket which is created below the drape at the location of the patient's feet which pocket is open on three sides. Moreover, the existence of this dead-air space disadvantageously provides the means for the above-described loss of surgical instruments during surgery.

Another disadvantage of the prior art Mayo-stand drape is that the conventional steel tray is not compartmentalized and, therefore, the placement of the surgical instruments thereon does not provide for adequate separation and proper placement of the surgical instruments.

Accordingly, an object of the present invention is to provide a Mayo-stand drape which is completely disposable and which includes a pre-formed compartmentalized tray portion that allows the proper placement therewithin of surgical instruments with the compartmentalization being in accordance with their shape and use. Such a compartmentalized tray will allow for improved orderliness of the instruments placed therewithin and improved recognition of the surgical instruments by the operating nurse that assists the surgeon, thereby allowing the nurse to more quickly and conveniently pick up the necessary instrument and hand the same to the surgeon. A specialized compartmentalized tray also prevents the instruments from becoming disarrayed during surgery.

Another object of the present invention is to provide a disposable Mayo stand surgical drape with one or more flap means to close off any open space between the Mayo stand and the draped body of the patient being operated upon.

The above-stated objects as well as other objects which, although not specifically stated, but are intended to be included within the scope of the present invention, are accomplished by the present invention and will become apparent from the hereinafter set forth Detailed Description of the Invention, Drawings, and the claims appended herewith.

SUMMARY OF THE INVENTION

The present invention accomplishes the above-stated objectives as well as others, as may be determined by a fair reading and interpretation of the specification, drawings, and claims appended hereto. The present invention comprises a disposable Mayo-stand drape which includes a built-in instrument tray and one or more flaps attached to the drape at one or more sides of the built-in surgical instrument tray. The flaps cover the space between the bottom of the Mayo-stand drape and the top of the body of the patient lying thereunder and thereby eliminates an opening or a pocket within which surgical instruments may inadvertently become lost.

Preferably, the built-in surgical tray is made to fit within the frame of the Mayo stand or it may be made to fit within a metal tray which is already fitted to the frame of the Mayo stand. The surgical tray may or may not have raised edges. The surgical tray may be compartmentalized but relatively shallow so as to allow the assisting nurse to easily grasp any of the instruments contained within the compartmentalized tray. The tray itself may be made of any number of low cost materials suitable for forming or embossing a disposable compartmentalized surgical tray within the surgical drape itself. For example, the tray may be made from a relatively firm thin film of plastic or compressed and formed by layers of the material from which the drape itself is made, or an inexpensive material, such as styrofoam, bonded to the material from which the surgical drape is made. However the disposable tray is made sufficiently rigid to be able to be used with or without the support or presence of an under metal tray fitted to the horizontal topside frame of a Mayo stand.

The flaps surrounding the compartmentalized tray may be secured to the main drape covering the lower portion of the body of the patient and thereby provide, in combination, one continuous, uninterrupted body drape having no pockets or openings where surgical instruments may become lost or entrapped.

BRIEF DESCRIPTION OF THE DRAWINGS

Various other objects, advantages, and features of the invention will become apparent to those skilled in the art from the following discussion taken in conjunction with the following drawings, in which:

FIG. 1 schematically illustrates a typical arrangement of a surgical table with an undraped Mayo stand fitted around the bottom portion thereof;

FIG. 2 comprises an isometric view of a typical Mayo stand provided with a typical prior art Mayo-stand drape;

FIG. 3 is a schematic illustration of an unfolded disposable Mayo-stand drape provided by the present invention;

DESCRIPTION OF THE PREFERRED EMBODIMENTS

Figure 4:
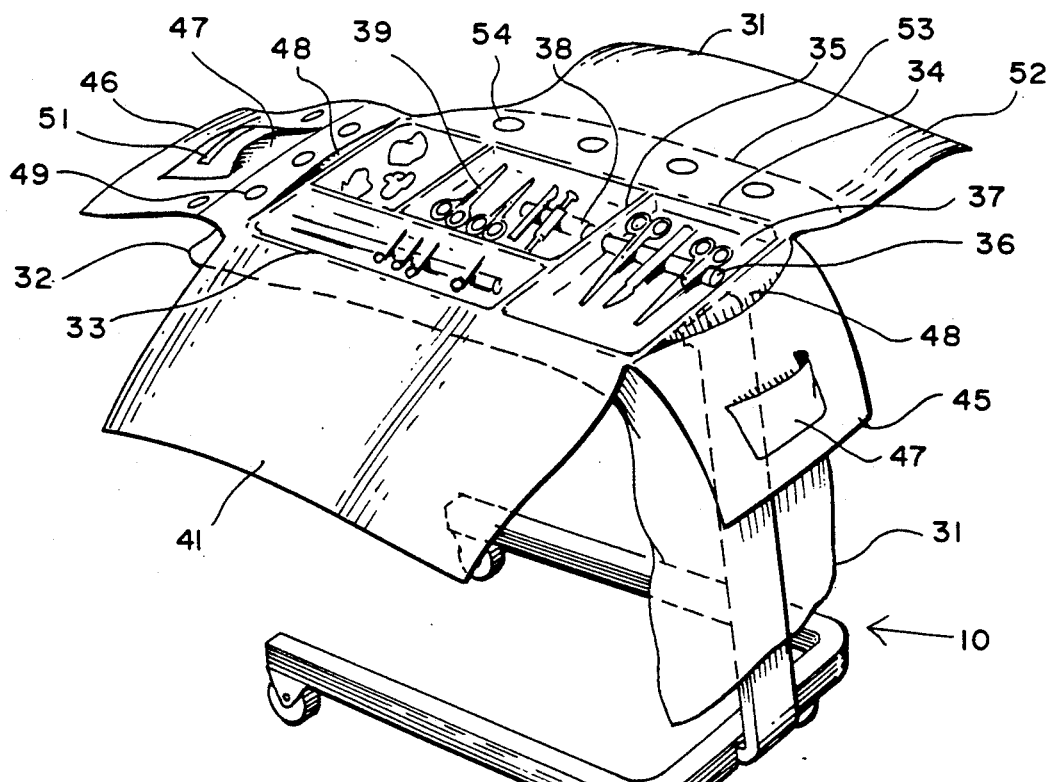
FIG. 4 illustrates the use of the inventive surgical drape of FIG. 3 as fitted to a Mayo stand.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings, wherein like characteristics and features of the present invention shown in the various figures are designated by the same reference numerals.

Reference is now made to FIGS. 1 and 2 of the drawings, which together illustrate a typical Mayo stand 10 in combination with a typical surgical or operating table 11 with which the Mayo stand 10 is utilized. The Mayo stand 10 includes a horizontal tray portion 13, a vertical support portion 14, and a horizontal leg portion 15. Tray portion 13 includes a horizontal frame 16 and a tray 17 which fits within frame 16. A small lip 18 around the exterior portion of tray 17 provides a support for the tray 17 when fitted within frame 16. Vertical support portion 14 comprises a vertical support member 18 structurally connected at one end to one side of frame 14 and at the other end to the closed portion 19 of legs 21. In a side view, it may thus be seen that Mayo stand 10 has a shape approximating that of a "C," which shape provides for fitting of the Mayo stand 10 at the foot end of the surgical table 11 with the tray portion 13 thereof fitting directly over the table's foot end. Wheels 22 attached to legs 21 provide for maneuverability of the Mayo stand 10.

The "C" shape of Mayo stand 10 also allows for covering of the tray portion 13 and the vertical support portion 14 of Mayo stand 10 by a sterilized surgical drape. For reference, the drape 23 shown in FIG. 2 is a prior art drape which typically comprises an elongated bag fabricated in a tubular construction with an open first end 24 and a closed second end 25. The construction of the prior art drape 23 thus provides for covering the tray portion 13 and the vertical support portion 14 of a typical Mayo stand 10. In this manner, any portion of Mayo stand 10 associated with the surgical procedure is covered by a sterile drape. However, the tubular-bag construction of the prior art drape 23 covers the tray 17 within frame 16 and to some extent hampers the functionability of tray 17 because of the tendency of the drape 23 to "bridge" over the functionally raised edges of tray 17. The bridging of the prior art drape 23 thereby obscures the raised edges of the tray which tends to negate functionability of the tray.

Figure 5:
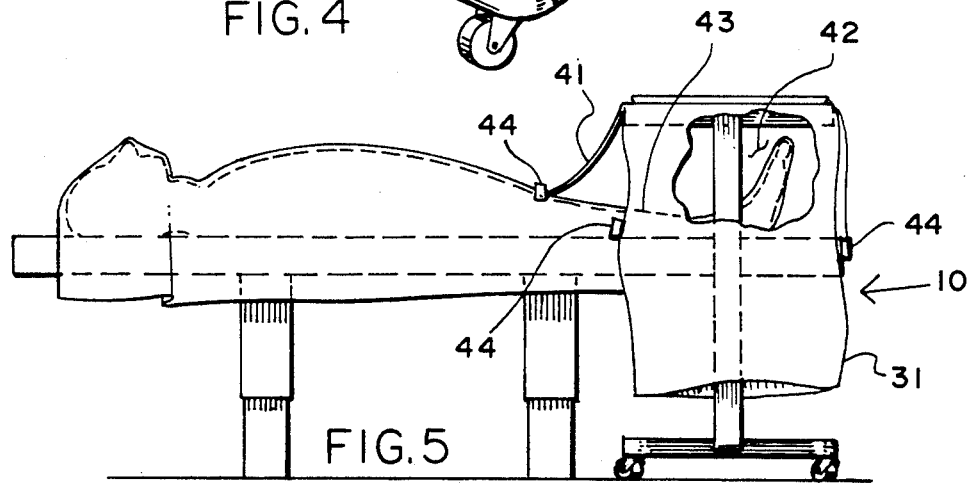
FIG. 5 is a side view of the inventive drape fitted to a Mayo stand with the Mayo stand arranged at the foot portion of a surgical table illustrating the covering of openings or pockets by the unfolded flaps; and, FIG. 6 is an end view of the arrangement of FIG. 5 further illustrating the coverage provided by the flaps of the present invention.
Figure 6:
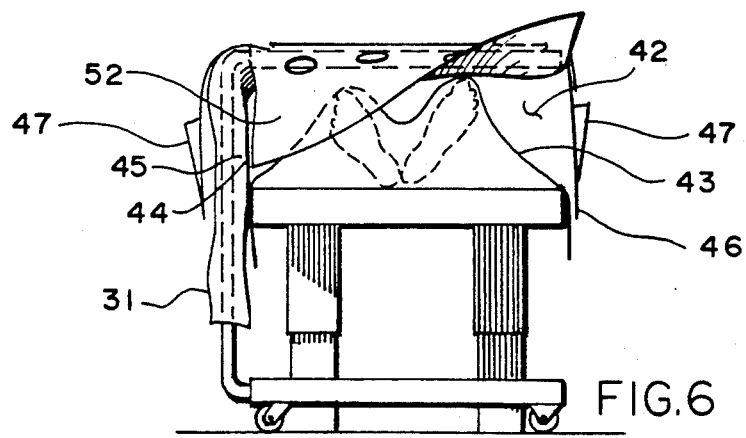

As can be seen in FIGS. 1, 5 and 6, an open space 42 or a pocket exists beneath the tray portion 13 of Mayo stand 10 and the foot portion of surgical table 11. Open space 42 is an undesirable feature of the prior art in that it provides for a location where instruments and other surgical apparatus may inappropriately gravitate where the instruments become lost.

One embodiment of the inventive Mayo-stand drape 31 is shown in FIG. 3 of the drawings. The elongated tubular construction of the inventive drape 31 is somewhat similar to that of the prior art drape 23. This is so in the sense that the inventive drape 31 is, in part, comprised of a tubular construction so as to be placed over the tray portion 13 and vertical support portion 14 of a Mayo stand 10. FIG. 4 shows the inventive Mayo-stand drape 31 applied to a Mayo stand 10.

A closed end portion 32 of the inventive drape 31 includes a formed and compartmentalized tray 33. Tray 33 includes a flanged lip 34 therearound so as to form an actual tray within and integral with the Mayo-stand drape 31. The formed tray 33 may preferably comprise a formed sheet of rigid plastic. Or, formed tray 33 may be made from a plurality of stacked layers of material, such as paper, from which the drape 31 is made so as to allow formation of a tray shape with the flanged lip 34 thereon as shown in FIG. 3 of the drawings. Further, the formed and tray 33 of drape 31 may be made from any other appropriate material, such as rigid styrofoam, which may then be adhesively secured to the Mayo-stand- drape 31.

The flanged lip 34 around the peripheral edges of tray 33 allows tray 33 to fit within and be supported by the frame structure 16 of Mayo stand 10. Or, the flanged lip 34 of tray 33 allows tray 33 to fit within the permanent tray 17 provided with a Mayo stand 10. Thus, tray 33 should be sufficiently stiff to support itself and the weight of a plurality of surgical instruments which it is required to contain.

Tray 33 may be compartmentalized by means of intersecting raised ribs 35 to form separate compartments within tray 33. Or, the lower planar surface 36 of tray 33 may be formed with a plurality of depressions to create separate compartments within the tray. The shape of each of the compartments 37 of tray 33 may be proportioned consistent with the shape of the surgical instruments to be stored therewithin. In this manner, like instruments may be placed side-by-side together in the same compartment 37 within tray 33. The compartmentalized aspect of tray 33 allows a nurse assisting the operating surgeon to quickly locate the instrument he or she is seeking to subsequently hand to the surgeon much more quickly than if tray 33 were not compartmentalized. The compartmentalization of tray 33 also insures that the surgical instruments therewithin are maintained in an orderly placement through the length of the surgery, even if the tray 33 is inadvertently bumped during movement of the Mayo stand or during the surgical procedure. An elevated projection 38 may be provided within one or more of the compartments 37 for placing instruments 39 therewithin, such as hemostats, with one end in a raised position and the other end in a lower position so as to allow more easy grasping of each of the instruments by the assisting nurse. The compartments 37 formed by ribs 35 and lip 34 should be relatively shallow so that the nurse may easily grasp the surgical instrument that he or she is attempting to grasp. Too deep of a compartment 37 may hamper the grasping of an instrument therewithin.

The compartmentalized arrangement of tray 33 may be consistent with the specific surgical specialty being conducted during the operation. For example, orthopedics, general surgery, gynecology, obstetrics, and other specialties, such as eyes, ears, nose and throat, each require special and different sized surgical instruments. The compartmentalized sections 37 of tray 33 would then be shaped so as to correspond to the particular surgical instruments being required for each of these specialties.

In a preferred embodiment of the invention, a first flap 41 is attached transversely to drape 31 immediately adjacent to the leading flanged lip 34 of tray 33. Flap 41 is intended to cover the entrance to the opening or pocket 42 comprising the space between the tray 33 of Mayo stand 10 and the upper surface of the draped 43 body of the patient being operated upon (see FIGS. 5 and 6). The free end of flap 41 may be removably attached to the surgical drape 43 covering the body of the patient by means of standard surgical clips 44 as are commonly known in the art. Flap 41 thereby effectively covers the front entrance to opening 42 which exists between the Mayo stand 10 and the top surface of the foot portion of the body of the patient being operated upon. This coverage serves to prevent any surgical instruments placed on the draped body of the patient after use, from gravitating downward into opening 42 and thereafter becoming lost.

Other flaps, such as side flaps 45 and 46, may also be attached to the inventive Mayo-stand drape 33 immediately adjacent to the side lips 34 of tray 33. Side flap 46 provides coverage of the side entrance to open space 42 between the Mayo stand and the body of the patient. Side flap 46 may also be removably attached to the body drape of the patient by clips 44. Side flaps 45 and 46 may also include a small pocket 47 and/or a large pocket 48. Pockets 47 and 48 may be utilized as a waste receptacle for any debris generated during the surgical procedure. Or, side flaps 45 and 46 may be provided with holes 49 and straps 51 which may be used for supporting other surgical apparatus.

A remote or back end flap 52 may also be provided with the inventive Mayo-stand drape 31 to cover the back entrance to open space 42 between the remote or back ends of Mayo stand 20 and surgical table 11. Also, a short and relatively stiff ledge-like flap 53 may be provided at the remote end of Mayo-stand drape 31, which ledge-like flap 53 may be utilized for positioning of holes 54 therethrough for locating and supporting various and somewhat heavy irrigation aspiration apparatus as may be used during the surgical procedure.

Figure 7:
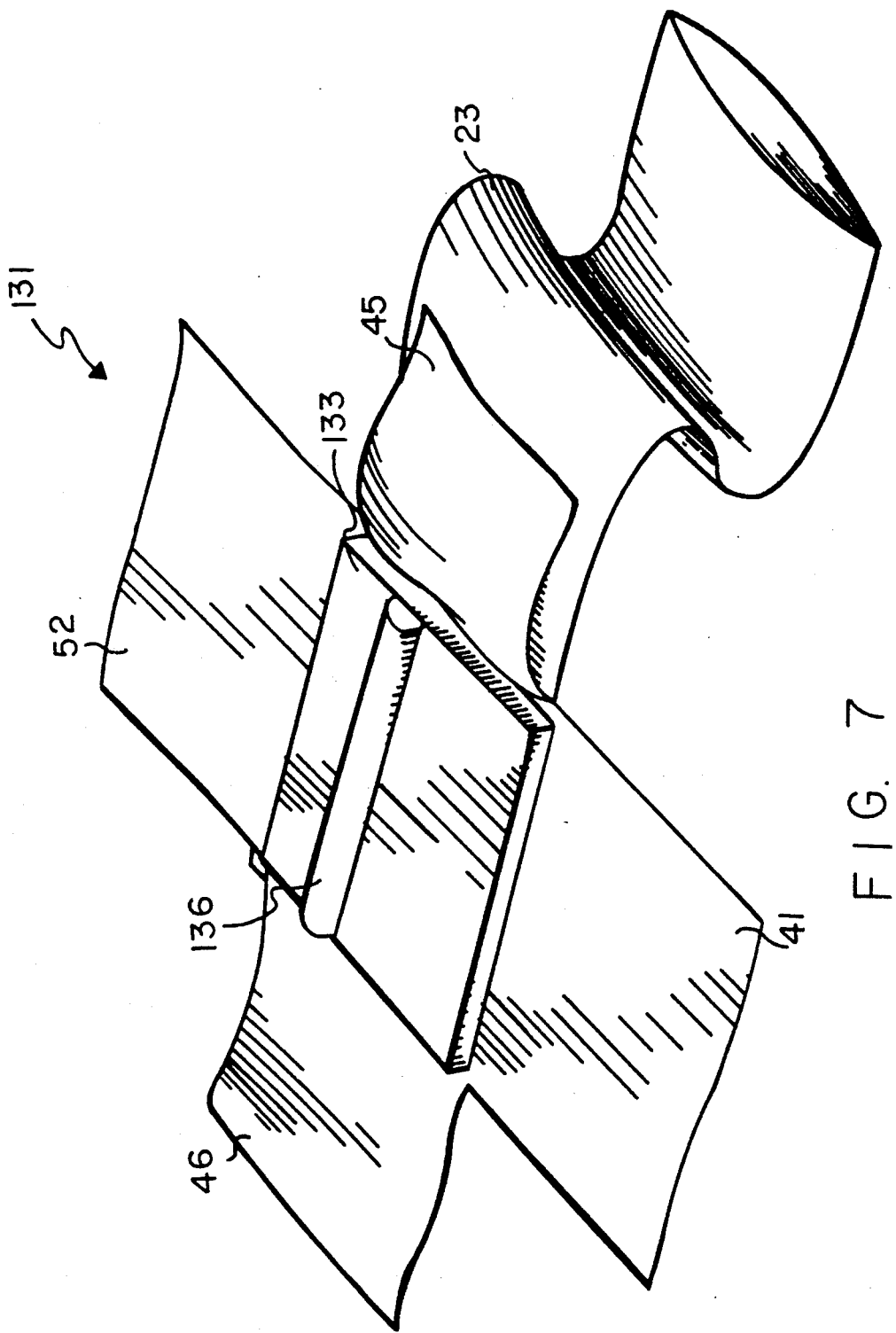
FIG. 7 is an isometric view of a tubular Mayo-stand drape having a flat tray attached thereto at the approximate closed end of the drape.

The embodiment shown in FIG. 7 is a simplified version of the drape 10 shown in FIGS. 2-6. In this embodiment, the Mayo-stand drape 131 includes the prior art drape 23 modified to include a tray means 133 and flap means 41, 46, 52, and 45. Tray means 133 comprises a flat sheet of an appropriate material such as those described in the embodiment of FIGS. 3 and 4. However, no raised peripheral edges are used. A raised portion 136 is provided on tray 133 to provide a stand against which surgical instruments may be placed in the same manner as elevated projections 36 and 38 of the prior embodiment. Flaps 41, 46, 52, and 45 are used in this embodiment of FIG. 7, as in the prior embodiment of FIGS. 2-6.

Thus, as explained above, the basic aspects of the inventive Mayo-stand drape 31 is to provide a built-in and compartmentalized instrument holding tray 33 and a plurality of flaps attached to the drape at the edge of tray 33 to cover entrances of an opening between the underside of a Mayo stand and the upper draped body of a patient being operated upon.

While the invention has been described, disclosed, modifications which it has assumed in practice, the scope of the illustrated and shown in certain terms or certain embodiments or invention is not intended to be nor should it be deemed to be limited thereby and such other modifications or embodiments as may be suggested by the teachings herein are particularly reserved especially as they fall within the breadth and scope of the claims here appended.

I claim as my invention:

1. A disposable drape for a surgical instrument stand comprising:
an elongated tube having an elongated axis made of a flexible material closed at a first end and opened at a second opposite end; and flap means, of a single thickness, attached near the closed end of said tubular drape for covering a space between a leading transverse edge of said tubular drape and a draped body of a patient lying on a surgical table located beneath said surgical instrument stand, said flap means being attached to an edge of said elongated tube, said edge extending parallel to said elongated axis, said flap extending away from said edge in a direction perpendicular to said elongated axis.

2. The disposable drape of claim 1, including means forming part of said tubular drape for positioning thereon surgical instruments when said tubular drape is positioned to cover said surgical instrument stand.

3. The disposable drape of claim 2, wherein said tray means comprises a tray built in to said drape.

4. The disposable drape of claim 3, wherein said tray is a compartmentalized to form two or more compartments.

5. The disposable drape of claim 4, wherein said compartments are formed by raised ribs.

6. The disposable drape of claim 4, wherein said compartments are formed by depressions formed into a bottom surface of said tray.

7. The disposable drape of claim 4, wherein at least one of said compartments include a raised portion extending along a length of said compartment.

8. The disposable drape of claim 2, wherein said means for positioning thereon surgical instruments comprises a rectangularly proportioned plate having at least one raised portion extending along an upper surface thereof.

9. The disposable drape of claim 1, wherein said flap means comprises a plurality of flaps each attached to said tubular drape at a location approximating an extending edge of said instrument tray, each flap having an approximate rectangular shape and extending away from said attachment to said tubular drape.

10. The disposable drape of claim 9, including a pocket formed into a flap of said drape.

* * * * *